United States Patent
Escames Rosa et al.

(10) Patent No.: US 10,092,544 B2
(45) Date of Patent: Oct. 9, 2018

(54) COMPOSITION COMPRISING MELATONIN OR ITS DERIVATIVES WITH COENZYME Q10 AND USE THEREOF AGAINST AGEING OF THE SKIN

(71) Applicant: UNIVERSIDAD DE GRANADA, Granada (ES)

(72) Inventors: Germaine Escames Rosa, Granada (ES); Darío Acuña Castroviejo, Granada (ES); Luis Carlos López Garcia, Granada (ES)

(73) Assignee: Universidad de Granada, Granada (ES)

( * ) Notice: Subject to any disclaimer, the term of this patent is extended or adjusted under 35 U.S.C. 154(b) by 0 days.

(21) Appl. No.: 14/648,148

(22) PCT Filed: Nov. 26, 2013

(86) PCT No.: PCT/ES2013/070817
§ 371 (c)(1),
(2) Date: May 28, 2015

(87) PCT Pub. No.: WO2014/083227
PCT Pub. Date: Jun. 5, 2014

(65) Prior Publication Data
US 2015/0306072 A1    Oct. 29, 2015

(30) Foreign Application Priority Data

Nov. 28, 2012 (ES) ................... 201231849

(51) Int. Cl.
| | | |
|---|---|---|
| *A61K 31/4045* | (2006.01) |
| *A61K 31/122* | (2006.01) |
| *A61K 8/35* | (2006.01) |
| *A61K 8/49* | (2006.01) |
| *A61K 9/00* | (2006.01) |
| *A61Q 17/04* | (2006.01) |
| *A61Q 19/08* | (2006.01) |

(52) U.S. Cl.
CPC ............ *A61K 31/4045* (2013.01); *A61K 8/35* (2013.01); *A61K 8/355* (2013.01); *A61K 8/49* (2013.01); *A61K 8/492* (2013.01); *A61K 9/0014* (2013.01); *A61K 31/122* (2013.01); *A61Q 17/04* (2013.01); *A61Q 19/08* (2013.01); *A61K 2800/78* (2013.01)

(58) Field of Classification Search
CPC ........ A61Q 17/04; A61Q 19/08; A61K 8/492; A61K 31/4045; A61K 8/49; A61K 8/355; A61K 9/0014; A61K 31/122; A61K 8/35; A61K 2800/78
See application file for complete search history.

(56) References Cited

U.S. PATENT DOCUMENTS

| | | | | |
|---|---|---|---|---|
| 6,048,886 | A * | 4/2000 | Neigut ................ | A61K 31/122 514/412 |
| 2003/0167556 | A1 | 9/2003 | Kelley | |
| 2005/0271692 | A1* | 12/2005 | Gervasio-Nugent ....................... | A61K 8/0208 424/401 |
| 2006/0286046 | A1* | 12/2006 | Haber ............... | A61K 8/447 424/59 |

FOREIGN PATENT DOCUMENTS

| | | |
|---|---|---|
| WO | WO 03/077335 | 9/2003 |
| WO | WO 2007/099172 A1 | 9/2007 |
| WO | WO 2009/024360 | 2/2009 |

OTHER PUBLICATIONS

Ortho Molecular Products. "CoQ10". Retrieved on Aug. 25, 2016. Retrieved from the internet <URL: http://www.orthomolecularproducts.com/file.aspx?DocumentId=1541>.*
Galano et al. "Melatonin as a naturally ally against oxidative stress: a physiochemical examination." J. Pineal Res. 2011; 51:1-6.*
Behl, C. "Vitamin E protects neurons against oxidative cell death in vitro more effectively than 17-β estradial and induces the activity of the transcription factor NF-κB." J. Neural Transm. 2000; 107: 393-407.*
Bentinger et al. (2007) The Antioxidant Role of Coenzyme Q. Mitochondrion 7S: S41-S50.
Berneburg et al. (2005) Creatine Supplementation Normalizes Mutagenesis of mitochrondrial DNA as Well as Funcational Consequences. J. Invest. Dermatol. 125:213-220.
García-Corzo et al. (2013) Dysfunctional Coq9 Protein Causes Predominant Encephalomyopathy Associated with CoQ deficiency. Human Molecular Genetics 22(6): 1233-1248.
García-Corzo et al. (2014) Ubiquinol-10 Ameliorates Mitochondrial Encephalopathy Associated with CoQ Deficiency. Biochmica et Biophysica Acta (BBA) Molecular Basis of Disease 1842(7): 893-901.
Izykowska et al. (2009) Effect of Melatonin on Melanoma Cells Subjected to UVA and UVB Radiation in In Vitro Studies. In vivo 23:733-738.
López et al. (2012) Treatment of CoQ10 Deficient Fibroblasts with Ubiquinone, CoQ Analogs, and Vitamin C: Time- and Compound-Dependent Effects. PLoS One 5(7): e11897.
Quinzii et al. (2010) Coenzyme Q and Mitochondrial Disease. Dev. Disabil. Res. Rev. 16(2):183-188.
Reagan-Shaw et al. (2007) Dose Translation from Animal to Human Studies Revisted. FASEB 22:659-661.
Scaletta et al. (1972) A Fine Structural Study of Divalent Cation-mediated Epithelial Union with Connective Tissue in Human Oral Mucosa. Am. J. Anat. 133:431-454.
International Search Report issued by the International Searching Authority (ISA/O.E.P.M.) dated Mar. 21, 2014 in connection with International Application No. PCT/ES2013/070817.
Venegas et al. (2012) Extrapineal Melatonin: Analysis of its Subcellular Distribution and Daily Fluctuations. J. Pineal. Res. 52:217-227.

* cited by examiner

*Primary Examiner* — Doan T Phan

(74) *Attorney, Agent, or Firm* — Gary J Gershik; Cooper & Dunham LLP

(57) ABSTRACT

The invention relates to a composition comprising melatonin, a metabolite or derivative thereof and coenzyme Q10 and to use thereof for the production of a pharmaceutical or cosmetic composition for the treatment of the skin, said composition potentiating the movement of both molecules into the mitochondrion and facilitating percutaneous absorption, in which both the melatonin and the CoQ10 can reach all of the strata of the skin.

10 Claims, 3 Drawing Sheets ns and to produce a cosmetic or pharmaceutical composition, protective against mitochondrial damage caused by cellular ageing and other pathologies presenting with mitochondrial damage.

COMPOSITION COMPRISING MELATONIN OR ITS DERIVATIVES WITH COENZYME Q10 AND USE THEREOF AGAINST AGEING OF THE SKIN

RELATED APPLICATIONS

This application is a § 371 national stage of PCT International Application No. PCT/ES2013/070817, filed Nov. 26, 2013, designating the United States, and claiming priority of Spanish Patent Application No. P 201231849, filed Nov. 28, 2012, the contents of each of which are hereby incorporated by reference into this application.

DESCRIPTION

The present invention relates to use of a composition comprising melatonin, a derivative or a metabolite thereof, and coenzyme Q10 suitable for potentiating the movement of said molecules into the cell mitochondrion and protecting the skin against the damage caused by oxidative stress. Therefore, the invention could be comprised in the field of the pharmaceutical and cosmetic industry.

PRIOR STATE OF THE ART

The increase in the production of free radicals causes an increase in the stiffness of cell membranes and connective tissue due to cross linking. This leads to a decrease in blood supply to organs and tissues, with the subsequent decrease in the tissue perfusion. Free radicals inexorably damage the cell and mitochondrial function slowly decreases, not only due to the oxygen radicals (ROS) that are generated within the actual organelle, but also due to those it receives from the cytosol. As a result, the electron transport chain (ETC) and oxidative phosphorylation become inefficient, with the production of ATP decreasing. This energy deficiency reduces the mitochondrial defense capacity, which becomes more vulnerable to the attack of ROS, further decreasing the efficiency thereof. A vicious circle is thus closed which ends with cell apoptosis.

In addition, ionizing radiations, such as ultraviolet radiation (UVR), are clear examples of ROS inducers, responsible for oxidative damage and immune lesion of peripheral tissues such as the skin.

Melatonin is a neurohormone that is synthesized and metabolized in the skin, where it plays a very important role. Some of its functions are related to the antioxidant properties of melatonin and include protection against UV rays and X-rays, as well as to other oxidizing agents inducing oxidative damage in the skin, including surgical interventions and burns (Izykowska I et al., In Vivo 2009, 23:739-745). Particularly, melatonin is a strong protector against UV radiations, fundamentally against UVB radiations, which are the most noxious component of UV radiations. Exposure to both UV-B and UV-A induces melatonin metabolism with the subsequent increase in 2-hydroxymelatonin and in N1-acetyl-N2-formyl-5-methoxykynureneamine (AFMK). Furthermore, melatonin also activates the antioxidant cascade in the skin, reducing free radicals. This data suggests that melatonin can control the redox state through its antioxidant functions.

The coenzyme Q10 (CoQ10; ubiquinone) is a molecule that is fundamental for mitochondrial function. It acts like an electron carrier in the electron transport chain. The reduced form of CoQ10, or ubiquinol, is one of the most potent lipophilic antioxidants of cell membranes (Bentinger M et al., Mitochondrion 2007, 7, S41-550). Furthermore, CoQ10 is necessary for pyrimidine synthesis and can modulate apoptosis and mitochondrial uncoupling proteins.

CoQ10 increases mitochondrial function and is therefore useful in mitochondrial pathologies and in pathologies presenting with mitochondrial damage, such as neurodegenerative diseases (Parkinson's and Alzheimer's), as well as in cellular ageing.

Skin cells depend on mitochondrial activity to produce enough energy for cell proliferation, mitochondrial DNA replication, protein synthesis and other cellular activities to repair the damage caused by the environment. Mitochondrial function and ATP production in fibroblasts drop with exposure to UV radiations (Berneburg M et al., J Invest Dermatol 2005, 125:213-220). In other studies it has been demonstrated that levels of CoQ10 in the skin decrease with age. Therefore, the topical application of Cob10 could have very beneficial effects for the skin.

A number of papers have evaluated the efficacy of the administration of CoQ10 to normalize mitochondrial function (López L C et al., Plos One 2012, doi:10.1371/journal.pone.0011897); however, CoQ10 is a very lipophilic molecule that accumulates in the membrane and moves into the mitochondrion in very small amounts. Therefore, exogenous CoQ10 is primarily distributed in the lysosomes, endoplasmic reticulum and plasma membrane, and only a small amount moves into the mitochondrion. Furthermore, most of the CoQ10 that moves into the mitochondrion is trapped by the external mitochondrial membrane, not being available for the respiratory chain which is located in the internal mitochondrial membrane. The administration of CoQ10 does not increase levels of ATP in patients with a CoQ10 deficiency after one week of treatment.

Compositions for the treatment of ageing of the skin, comprising the mixture of several substances, and included among them are both melatonin and coenzyme Q10, have been claimed in various patents.

US patent application 2005/0025756 A1 describes the combination of CoQ10 and other chemical substances in a chemical composition causing an increase in the delivery of coenzyme Q10 into a cell, which enables overcoming the solubility problems thereof, being able to be absorbed by the cell more quickly.

Accordingly, there is a need for a tool that facilitates the movement of CoQ10 into the mitochondrion and potentiates the movement of melatonin into the mitochondrion, and thereby reverses the mitochondrial damage caused in cellular ageing as well as in many pathologies presenting with mitochondrial damage.

DETAILED DESCRIPTION OF THE INVENTION

The present invention describes a composition comprising melatonin or a derivative thereof, preferably at a concentration of 1.0 to 5.0% w/v, and CoQ10, preferably at a concentration of 0.2 to 1.5% w/v, for the production of a pharmaceutical or cosmetic composition for potentiating the movement of said molecules into the mitochondrion, and therefore use thereof for the treatment and/or prevention of ageing of the skin.

The examples of the following invention show in vivo results of the levels of these molecules in the cytosol and in the mitochondria of skin cells, as well as the plasma levels reached after application of the cream on the skin. The composition of the invention is useful for potentiating the movement of CoQ10 and melatonin into the mitochondrion and for favoring percutaneous absorption, assuring that the melatonin and CoQ10 reach all of the layers of the skin, epidermis and dermis. The present invention demonstrates that the combination of CoQ10 and melatonin increases the movement of both molecules into the cell, and primarily into the mitochondrion, allowing percutaneous absorption at the same time, which does not occur when creams with the individual compounds are applied.

The usefulness of the combination of melatonin, or its derivatives, and CoQ10 in the topical application on the skin, with a cell protection effect against oxidative stress, can be inferred from this earlier data. The topical application of melatonin+CoQ10 prevents cell function impairment as a result of mitochondrial damage caused by oxidative stress.

Therefore, a first aspect of the present invention relates to a composition (hereinafter "composition of the invention") comprising:
a. coenzyme Q10 (CoQ10), and
b. at least one compound of general formula (I),

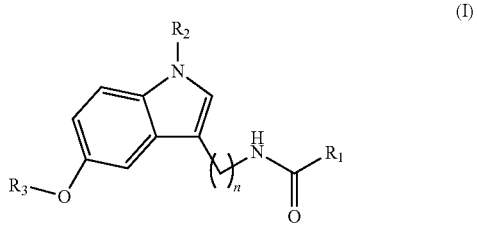

(I)

where:
n is an integer between 1 and 4; preferably 1, 2 or 3.
$R_1$ is a straight or branched ($C_1$-$C_4$) alkyl group;
$R_2$ is hydrogen, straight or branched ($C_1$-$C_4$) alkyl, a —C(=O)O—Ra group or a —C(=O)—N(H)—Ra group, wherein Ra is a straight or branched ($C_1$-$C_4$) alkyl group; and
$R_3$ is a hydrogen or a straight or branched ($C_1$-$C_4$) alkyl group.

The expression "melatonin, a metabolite or derivative thereof" is understood as any cosmetically or pharmaceutically acceptable compound that is comprised within general formula (I), as well as the salts, solvates or prodrugs thereof, and is useful for the production of a pharmaceutical or cosmetic composition with CoQ10 for potentiating the movement of this molecule into the mitochondrion and facilitating percutaneous absorption. Therefore, when the present invention refers to the compounds of general formula (I), the present invention also refers to the salts, solvates or prodrugs thereof. Therefore, the compounds of general formula (I) described above refer to melatonin, the metabolites or derivatives thereof.

The term "alkyl" herein refers to aliphatic, straight or branched chains, having from 1 to 4 carbon atoms, for example, methyl, ethyl, n-propyl, i-propyl, n-butyl, tert-butyl, sec-butyl, etc. Preferably the alkyl group has between 1 and 2 carbon atoms, and more preferably it is a methyl group.

In a preferred embodiment of the present invention $R_1$ is a methyl group and $R_3$ is hydrogen or a methyl group.

In another preferred embodiment n is 1.

Preferably in another embodiment $R_2$ is hydrogen.

In another preferred embodiment the compound of formula (I) is selected from melatonin or N-acetylserotonin. More preferably it is melatonin.

The term "melatonin" refers to N-acetyl-5-methoxytryptamine, also referred to in the literature as melatonin, melatonine, melatol, melovine, circadin, regulin, acetaminde, N-acetyl-methoxy-tryptamine, 5-methoxy-N-acetyltryptamine, N-[2-(5-methoxy-1H-indol-3-yl)ethyl]acetamide or N-[2-(5-methoxyindol-3-yl)ethyl]acetamide, or when in the compound of general formula (I) $R_1$ and $R_3$ are a methyl group, n is 1 and $R_2$ is hydrogen. The CAS number for melatonin is the 73-31-4.

Melatonin is an endogenous neurohormone produced by the pineal gland (epiphysis cerebri), as well as by other organs and tissues, such as the gastrointestinal tract, the retina, lymphocytes and cells of the bone marrow, and the skin, for example, in a physiological manner in animals, inter alia, in humans.

Melatonin is produced in animals, inter alia, humans, from serotonin (5-hydroxytryptamine, 5-HT), which in turn derives from the amino acid tryptophan. Therefore, the present invention could also relate to use of a composition comprising any of the melatonin precursors (5-HT, tryptophan or intermediate metabolites such as N-acetylserotonin, or NAS), at a sufficient concentration so that in the human body they are transformed into melatonin at the concentrations described in the present invention, for the production of a pharmaceutical composition with CoQ10 for potentiating the movement of this molecule into the mitochondrion and facilitating percutaneous absorption.

In addition, the present invention also relates to the pharmaceutically acceptable salts of melatonin or of its derivatives which can be generated by means of chemical processes known by the person skilled in the art, for example, by means of a reaction with an acid in water or in an organic solvent or in a mixture of both. Ether, ethyl acetate, ethanol, isopropanol or acetonitrile can be used as an organic solvent. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanesulfonate and p-toluenesulfonate.

The term "prodrug", as it is used herein, relates to a chemical compound that has experienced a chemical derivation, for example, a substitution or an addition of an additional chemical group, to modify any of its physico-chemical properties, such as solubility or bioavailability, but which does not modify the technical characteristics of the original molecule. A prodrug may be, for example, an ester, ether or amide derivative. Bioavailability relates to the availability thereof in a specific biological compartment.

The term "solvate" according to this invention must be understood as that derivative of melatonin that has another molecule, for example, a polar solvent, attached by means of a non-covalent bond. The examples of such solvates include hydrates and alcoholates, for example, methanolates.

The preparation of solvates and prodrugs can be carried out by means of methods known in the state of the art.

Non-pharmaceutically acceptable salts, solvates or prodrugs are also within the scope of the invention since they can be useful in the preparation of pharmaceutically acceptable salts, solvates or prodrugs.

The composition of the invention can also relate to a composition comprising a functional biological equivalent of melatonin at a concentration which is equivalent to that described in the compositions of the invention.

The term "functional biological equivalent" or "bioequivalent variable", as it is used herein, refers to a molecule with the same function as the described molecule, which can have slight variations with respect to the described molecule without said variations providing any added technical effect for said molecule. The present invention therefore refers to melatonin variants having the same function and having slight variations without said variations providing any added technical effect for melatonin.

"Concentration that is equivalent" is understood as that concentration necessary for the functional biological equivalent of melatonin to produce the same effect as that described in the present invention for the composition of the invention.

Melatonin is also produced in plants. For example, the presence of melatonin has been described in algae, edible plants, cereals, fruits, seeds, roots, stems, leaves and medicinal herbs. For example, the presence of melatonin has been described in cocoa, coffee, grapes, tomatoes, green tea, algae, cereals and olives, so the origin of the melatonin of the composition of the invention can be from a plant origin. Obtaining the melatonin from a plant origin (also referred to as phytomelatonin) can be done by means of any method known by the person skilled in the art for such purpose.

The origin of the melatonin used in the composition of the invention can also be synthetic. Chemical synthesis of melatonin can be done by means of the techniques known by the person skilled in the art for such purpose.

The most common form of CoQ in humans is CoQ10, with the following structural formula:

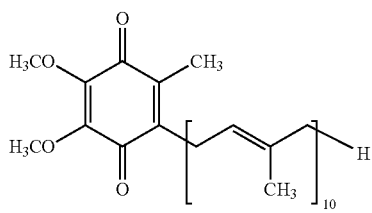

although small traces of CoQ9 can also be found. This molecule is also referred to as ubiquinone since it is produced by virtually all organisms with respiratory metabolism. It is a fat-soluble benzoquinone. The "Q" refers to the quinone chemical group, and the "10" refers to the number of isoprenoid subunits it has. The benzoquinone portion of CoQ10 is synthesized from tyrosine, whereas the isoprenoid chain is synthesized from acetyl-CoA through the mevalonate pathway. The various types of coenzyme Q can be distinguished by the number of isoprenoid chains they have.

In another preferred embodiment, the composition of the invention comprises a compound of formula (I), preferably melatonin, at a concentration of 1 to 5% w/v with respect to the final composition, more preferably at a concentration of 1.5 to 3% w/v with respect to the final composition, and even more preferably at a concentration of about 2% w/v with respect to the final composition.

In another preferred embodiment, the composition of the invention comprises CoQ10 at a concentration of 0.2 to 1.5% w/v with respect to the final composition, more preferably at a concentration of 0.3 to 1.0% w/v with respect to the final composition, and even more preferably at a concentration of about 0.5% w/v with respect to the final composition.

In another preferred embodiment, the composition of the invention comprises a compound of formula (I), preferably melatonin, at a concentration of 1.0 to 5.0% w/v, plus CoQ10 at a concentration of 0.2 to 1.5% w/v.

"Concentration of 1 to 5% w/v" is understood as the composition comprising from 1 to 5 grams of the compound of formula (I), preferably melatonin, in 100 ml of final composition.

"Concentration of 0.2 to 1.5% w/v" is understood as the composition comprising from 0.2 to 1.5 grams of CoQ10 in 100 ml of final composition The abbreviation "w/v" refers to weight/volume or mass/volume (m/v).

In a particular embodiment, the composition of the invention comprises at least one antioxidant.

The term "antioxidant" refers to that substance that is able to delay or prevent oxidation, particularly of the compound of general formula (I) and more particularly of melatonin. Antioxidizing agents known in the state of the art can be used as antioxidizing agents, for example, but without being limited, the list comprising tocopherol, ascorbic acid, sodium ascorbate, tartaric acid, butylhydroxyanisole, citric acid, vitamin A and vitamin E.

In a more particular embodiment of the preceding one, the antioxidant is at a concentration of 0.25 to 0.75% w/v with respect to the final composition. More preferably the concentration is from 0.40 to 0.60% w/v with respect to the final composition.

In another particular embodiment of the composition of the invention it furthermore comprises at least one preservative.

"Preservative" is understood as that substance maintaining the properties of the cosmetic or medicinal product by inhibiting contamination by germs; it can be an ionic or non-ionic preservative. The preservative used will not be toxic, will be chemically stable and compatible with both the compound of formula (I), particularly melatonin, and with CoQ10. The preservative is preferably at a concentration of 0.4 to 1% w/v with respect to the final composition. Preservative agents known in the state of the art can be used as preservative agents, for example, but without being limited, the preservative can refer to benzoic acid, sodium benzoate, ascorbic acid, potassium sorbate, methylparaben, ethylparaben or butylparaben. "Germs" are understood as any cell that can grow and multiply in the composition of the invention, for example, bacteria, fungi and yeasts.

Another particular embodiment of the composition of the invention furthermore comprises at least one gelling agent. The gelling agent is preferably at a concentration of 2.5 to 7% w/v with respect to the final composition.

The term "gelling agent" refers to a substance that forms a gel, i.e., a three-dimensional network formed by the gelling agent and generally containing a liquid phase. The gelling agents that can be used can be those known by the person skilled in the art for the production of a pharmaceutical or cosmetic composition. Preferably the gelling agent is selected from the list comprising polyethylene and polypropylene copolymer, cellulose and guar gum.

In a particular embodiment, the composition of the invention furthermore comprises at least one "pharmaceutically and/or cosmetically acceptable vehicle", which refers to those substances, or combination of substances, known in the pharmaceutical and/or cosmetic sector used in the production of cosmetic and/or pharmaceutical forms of administration and includes, but without being limited, solids, liquids, solvents or surfactants. The vehicle can be an inert substance or a substance having an action that is analogous to any of the compounds of the present invention. The vehicle is preferably at a concentration of 2.5 to 7% w/v with respect to the final composition. The function of the vehicle is to facilitate incorporation of the expression product of the invention, as well as also other compounds, to allow better dosing and administration or to provide consistency and form to the pharmaceutical composition. When the presentation form is liquid, the vehicle is the diluent. These vehicles can be known by the person skilled in the art, for example, lysosomes, millicapsules, microcapsules, nanocapsules, sponges, millispheres, microspheres, nanospheres, milliparticles, microparticles and nanoparticles.

In a particular embodiment, the composition of the invention further comprises at least one pharmaceutically and/or cosmetically stable excipient or adjuvant. The excipient is preferably at a concentration of 1 to 5% w/v with respect to the final composition.

The term "excipient" refers to a substance which aids in the absorption of the pharmaceutical or cosmetic composition of the invention, stabilizes said compositions or aids in its preparation in the sense of giving it consistency or providing flavors making it more pleasant. Therefore, the excipients may have the function of keeping the ingredients bound to one another, such as starches, sugars or celluloses, for example, a sweetening function, a colorant function, a medicinal product protection function, such as insulating it from the air and/or moisture, for example, a filler function of a pill, capsule or any other presentation form, such as dibasic calcium phosphate, for example, a disintegrating function for facilitating dissolution of the components and absorption thereof into the intestine, without excluding another type of excipients not mentioned in this paragraph, for example starches, sugars or celluloses. In order for the composition of the invention to have a pleasant flavor, an essence, such as essence of cinnamon, lemon, orange, mandarin or vanilla, for example, can be added.

The term "adjuvant" refers to any substance potentiating the response of an active ingredient. In the present invention it refers to any substance potentiating the effects of the composition of the invention; it can refer to any adjuvant known by the person skilled in the art.

The term "pharmaceutically and/or cosmetically acceptable" refers to the compound to which reference is made being allowed and evaluated such that it does not cause damage to the organisms to which it is administered.

In another particular embodiment, the composition of the invention furthermore comprises at least other additives such as an emulsifier, an emollient or an antifoaming agent. In the composition of the invention each of these additives can individually be at a concentration of 2.5 to 7% w/v with respect to the final composition. Therefore, said particular composition refers to a composition comprising between 2.5 and 7.0 grams of additive in 100 ml of total volume of the final composition.

"Emulsifier" is understood as those substances the function of which is to stabilize mixtures of two immiscible liquids. The list of emulsifiers of the particular embodiment includes Montanov 68, glycerol, sodium lauroyl glutamate, sodium cocoyl glutamate, PEG-26 jojoba acid, PEG-26 jojoba alcohol, PEG-11 avocado glycerides, PEG-30 almond glycerides, caprylic compound and triethylhexanoin.

"Emollient" is understood as a complex mixture of chemical agents particularly designed to act at different levels in epidermal strata, for softening and slackening tissue. The action thereof can be superficial or deep, according to if the composition remains on the surface of the skin or if it is absorbed. The emollient for the particular embodiment can be selected from the list comprising perhydrosqualene, lanolin, petroleum jelly, rosehip oil, borage oil, sweet almond oil, peach kernel oil, olive oil, beeswax, paraffin waxes, stearyl alcohol and cetyl alcohol.

"Antifoaming agent" is understood as an additive used in the cutting fluids to aid in preventing foaming and bubbling, and to thus improve the cooling capacity of the fluid. They are products with low viscosity and ease for being quickly propagated on surfaces with effervescence where they destabilize the foam films, which causes the air bubbles to burst and the breakdown of the foam of the surface. The antifoaming agent of this particular embodiment is selected from the list comprising dimethicone, dimethiconol, phenethyl disiloxane, tetramethyl decynediol, phenyl trimethicone, polysilicone 7, isopropyl alcohol, hexyl alcohol, propyl alcohol, hexamethyl-disiloxane, bisphenyl hexamethicone and trimethyl-siloxy silicate.

In another particular embodiment, the composition further comprises at least one antimicrobial agent.

The term "antimicrobial agent" describes a substance acting against parasitic microorganisms such as bacteria, viruses, or fungi, by killing them or inhibiting their growth. The antimicrobial agent is selected from the list comprising phenonip (composition the main component of which is 2-phenoxyethanol), methylparaben, ethylparaben, butylparaben, propylparaben, methyl parahydroxybenzoate, propyl parahydroxybenzoate, benzalkonium chloride and imidazolidinyl-urea.

In an even more particular embodiment of the preceding embodiment, the antimicrobial agent is at a concentration of 0.4 to 1.0% w/v with respect to the final composition. In other words, said particular composition refers to the composition of the invention further comprising at least between 0.4 and 1.0 grams of additive in 100 ml of total volume of the final composition.

In another particular embodiment, the composition of the invention further comprises at least one agent acting as a filter of UV rays, preferably UV-B and/or UV-A rays. This is understood as those substances which aid in preventing sunburns and reduce the harmful effects of the sun, such as premature ageing of the skin and skin cancer. Among those most widely used, stand out zinc oxide, titanium dioxide, iron oxide, talc, silicates (clays, kaolin, bentonite), PABA (p-aminobenzoic acid) and derivatives, cinnamates, anthranilates, salicylates, benzophenones, dibenzoylmethane and benyzlidene-camphor.

The composition of the invention can be both a cosmetic composition and a pharmaceutical composition, and it can be formulated for administration in a range of forms known in the state of the art. Such formulations can be administered to an animal, and preferably to a mammal, and more preferably to a human, through a range of routes, including, but without being limited to topical route, oral route, parenteral route, intraperitoneal route, intravenous route, intradermal route, intralesional route, intraarterial route, intramuscular route, intranasal route, or subcutaneous route.

Based on what is herein described, another particular embodiment relates to use where the composition is presented in a form adapted for topical administration.

The term "topical administration" herein refers to the composition be administered on the skin.

A particular embodiment of the composition of the invention relates to use thereof in the form of a cream, lotion, gel or aerosol. In addition to the preceding formulations, the following can also be used in the composition of the invention: oil in water emulsions, water in oil emulsions, milks, lotions, gels, ointments, balsams, foams, body oils, soaps, bars, pencils, vaporizers, creams, liniments, salves, sera and mousses. The composition can also be incorporated in solid supports selected from the group consisting of hydrogels, wipes, patches and facial masks.

In another particular embodiment, the composition of the invention is in the form of an emulsion. "Emulsion" is understood as a more or less homogenous mixture of immiscible liquids. One liquid (the dispersed phase) is dispersed in another one (the continuous phase or dispersing phase). The emulsion of the invention is an O/W (oil/water) emulsion which is described as the dispersed phase being an oily phase and the dispersing phase being an aqueous phase.

In another particular embodiment, the composition of the invention corresponds with a pharmaceutical or cosmetic composition.

"Cosmetic composition" or "cosmetic" is understood as any substance or mixture intended for being placed in contact with superficial parts of the human body (epidermis, hair and capillary system, nails, lips, and external genital organs) or with the teeth and buccal mucosae, for the exclusive or primary purpose of cleaning them, perfuming them, changing their appearance, protecting them, keeping them in good condition or correcting body odors.

The term "pharmaceutical composition" or "medicinal product" refers to any substance used for the prevention, diagnosis, alleviation, treatment or curing of diseases in humans or animals. In the context of the present invention it refers to a composition capable of treating and/or preventing skin pathologies.

Another aspect of the invention relates to the use of the composition of the invention and of the compositions of the particular embodiments for the production of a medicinal product.

A particular embodiment of the aspects and preceding particular embodiments, as well as of the composition described in each of the particular embodiments, corresponds with the use thereof for the treatment and/or prevention of cellular senescence or of diseases presenting with cellular ageing. "Cellular senescence" is understood as the process initiated in response to stress and damage occurring in a cell, and it constitutes an alternative programmed cell death response pathway and is of vital importance for suppressing cancer cell formation. It is also associated with the repair of tissues and inflammation thereof, processes associated with tumor growth. The cellular senescence is therefore simultaneously associated with tumor suppression and promotion processes, like in the ageing and repair of tissues.

In a particular embodiment, diseases presenting with cellular ageing may therefore be tumors, cancers, inflammation of tissues, and more particularly those related to the skin.

In the present invention "treatment and/or prevention" refers to both therapeutic treatment and prophylactic treatment, or preventive measures. Those situations susceptible to treatment include those already associated with disorders as well as in those in which the disorder is prevented. A "disorder" is any condition that would benefit from treatment with the composition of the invention, as it is described herein.

Another aspect of the invention relates to a cosmetic method for anti-ageing of the skin, which is characterized by the topical application, preferably in the form of a cream or emulsion, of a therapeutically effective amount of the composition of the invention.

"Anti-ageing" herein refers to the process of slowing down, preventing or reversing the ageing process.

The expression "therapeutically effective amount" of the composition refers to the pharmaceutically or cosmetically effective amount of the composition that produces the desired effect, and it is generally determined, among other causes, by the characteristics typical of said pharmaceutical composition and of the therapeutic effect to be achieved. The dosage for obtaining a therapeutically effective amount depends on a range of factors, such as, for example, age, weight, sex or tolerance of the animal, preferably a mammal and more preferably human.

"Ageing of the skin" is a process related to the loss of fibrous of tissue, the slowing down of the cell turnover rate and decrease in glandular and vascular activity in cutaneous tissue. Changes in skin due to the ageing process are related to environmental factors, such as exposure to the sun, genetic constitution, nutrition, passage of time, inter alia. Changes in connective tissue reduce skin resistance and elasticity, causing unwanted effects in skin such as wrinkles, liver spots, among others known by any person skilled in the art.

In a particular embodiment of this aspect of the invention, ageing of the skin is caused by exposure of the skin to the sun's rays.

Therefore, another aspect of the present invention relates to a cosmetic composition comprising the composition of the invention, and more particularly said composition is a sunscreen, which preferably is a cream, lotion, gel, milk or oil.

Throughout the description and claims the word "comprises" and its variants do not seek to exclude other technical characteristics, additives, components or steps. For the persons skilled in the art, other objects, advantages and features of the invention will be inferred in part from the description and in part from the practice of the invention. The following examples and drawings are provided by way of illustration and do not intend to be limiting of the present invention.

EMBODIMENTS

Figure 1:
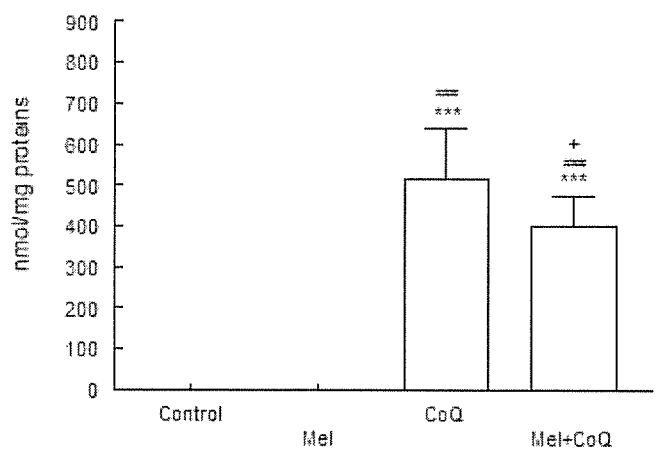
FIG. 1 shows levels of CoQ10 in cytosol of the skin of mice treated with cream comprising melatonin, cream comprising CoQ10, and cream comprising melatonin+CoQ10. Controls (C), mice treated with cream comprising melatonin (aMT), mice treated with cream comprising CoQ10 (CoQ), and mice treated with cream comprising melatonin+CoQ 10 (aMT+CoQ). ***$p<0.001$ compared to C; +$p<0.05$ compared to CoQ10, ###$P<0.001$ compared to melatonin.

The following examples provided in this patent document serve to illustrate the nature of the present invention. These examples are included only for illustrative purposes and must not be interpreted as limitations to the invention herein claimed. Therefore, the examples described below illustrate the invention without limiting the field of application thereof.

The invention will be illustrated below by means of tests performed by the inventors which clearly show the usefulness of the cream comprising melatonin plus CoQ10 for potentiating the movement of these compounds into cells, primarily into the mitochondrion, and favoring percutaneous absorption, allowing these compounds to reach all of the layers of the skin.

EXAMPLE 1

The following example provides formulations of cream comprising melatonin, cream comprising CoQ10 and cream comprising melatonin together with CoQ10 and the method of producing them:

Cream 1: Melatonin (aMT)

| PHASE A: 70° C. | Montanov 68 | 5% |
|---|---|---|
| | Perhydrosqualene | 5% |
| | Long-chain TG | 5% |
| | Dimethicone | 5% |
| | Phenopip | 0.80% |
| | Vitamin E | 0.50% |
| PHASE B: 75° C. | Glycerol | 5% |
| | $H_2O$ | qsf |
| | Melatonin | 2% in 30% PG |

Cream 2: CoQ10

| PHASE A: 70° C. | Montanov 68 | 5% |
|---|---|---|
| | Perhydrosqualene | 5% |
| | Long-chain TG | 5% |
| | Dimethicone | 5% |
| | Phenopip | 0.80% |
| | Vitamin E | 0.50% |
| PHASE B: 75° C. | Glycerol | 5% |
| | $H_2O$ | qsf |
| | CoQ10 | 0.5% in 5% PG |

The solution comprising CoQ is added to the emulsion at 60° C.

Cream 3: CoQ10+aMT

| PHASE A: 70° C. | Montanov 68 | 5% |
|---|---|---|
| | Perhydrosqualene | 5% |
| | Long-chain TG | 5% |
| | Dimethicone | 5% |
| | Phenopip | 0.80% |
| | Vitamin E | 0.50% |
| PHASE B: 75° C. | Glycerol | 5% |
| | $H_2O$ | qsf |
| | Melatonin | 2% in 30% PG |
| | CoQ10 | 0.5% in 5% PG |

The solution comprising CoQ is added to the emulsion at 60° C.

where: TG triglyceride; PG propylene glycol.

The method for producing the creams 1, 2 and 3 was carried out by means of the following steps:

Cream 1:

PHASE A: all the components of phase A are mixed and it is heated until reaching the temperature of 70° C.

PHASE B: the 2% melatonin in 30% PG is prepared: 2 grams of melatonin are weighed and dissolved in 30 ml of PG for 100 ml of final composition. All the components are mixed and it is heated until reaching the temperature of 75° C.

Finally, phase B is added to phase A.

For creams 2 and 3, the method is the same as for cream 1.

Phase B is added to phase A. The solution comprising CoQ in PG is added when the temperature of this mixture reaches 60° C.

EXAMPLE 2

Each of the creams described in the preceding example was administered to experimentation animals by topical route. Nude male mice 3 months of age (Harlan) were used. The animals were independently housed in conventional cages in an animal facility conditioned for that purpose in the Centro de Investigación Biomédica (Biomedical Research Center), in sterile conditions and under a controlled light period (12:12 h) and temperature (22±1° C.) environment, and laboratory diet and water ad libitum. The study was conducted in samples of skin from the back of the mice.

The experimental groups included 6 mice each, and they were the following:

Control group (C)
Group treated with cream comprising 2% melatonin
Group treated with cream comprising 0.5% CoQ10
Group treated with cream comprising 2% melatonin+ 0.5% CoQ10

Application of the different formulations of the cream was done in the dorsal area at a ratio of 15 mg/cm$^2$/day (5 mg/cm$^2$/administration).

Administration of the cream in the different groups was done twice a day (every 12 hours). The animals were sacrificed a month after starting treatment.

Blood samples are taken before the animals are sacrificed. The animals are anesthetized with chloroform and 1 ml of blood is taken by means of cardiac puncture. Plasma is separated from the red blood cells, which is used to measure levels of melatonin. After taking the blood sample and sacrificing the animals, samples of skin are taken from the back by means of surgical dissection. The skin is placed in a Petri dish with phosphate-buffered saline. The adipose tissue is removed, cut into pieces, and frozen at −80° C. until analysis. The method for extracting the epidermis and the histochemical technique are based on the protocol described by Scaletta and MacCalum, (Am J. Anat. 133: 431-53, 1972).

These samples were used to evaluate levels of melatonin and CoQ10 in the cytosol and mitochondrion of the skin and in plasma.

Figure 2:
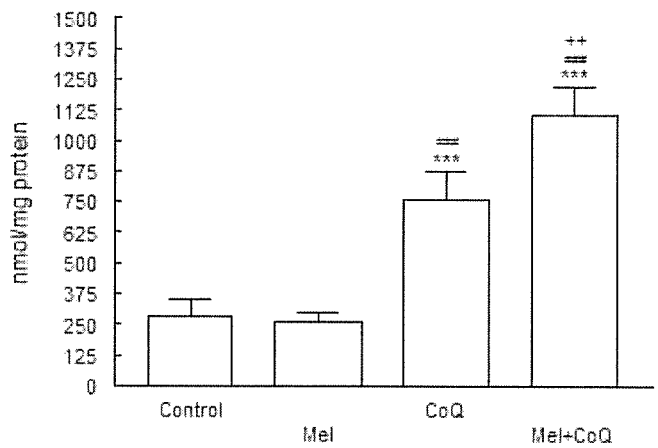
FIG. 2 shows levels of CoQ10 in mitochondrion of the skin of mice treated with cream comprising melatonin, cream comprising CoQ10, and cream comprising melatonin+CoQ10. Controls (C), mice treated with cream comprising melatonin (aMT), mice treated with cream comprising CoQ10 (CoQ), and mice treated with cream comprising melatonin+CoQ 10 (aMT+CoQ). ***$p<0.001$ compared to C; ++$p<0.01$ compared to CoQ10, ###$P<0.001$ compared to melatonin.
Figure 4:
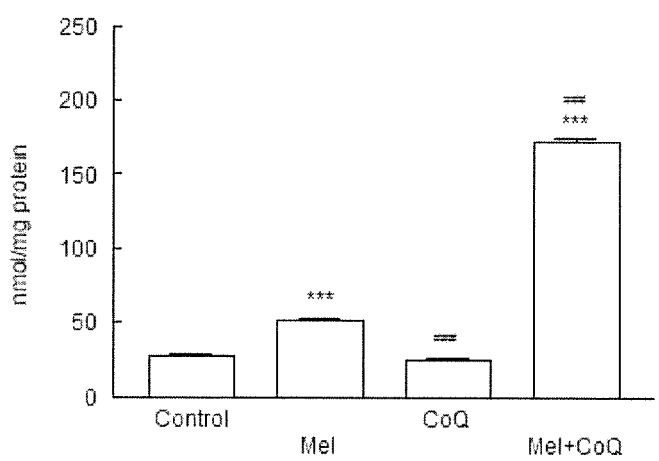
FIG. 4 shows levels of melatonin in cytosol of the skin of mice treated with cream comprising melatonin, cream comprising CoQ10, and cream comprising melatonin+CoQ10. Controls (C), mice treated with cream comprising melatonin (aMT), mice treated with cream comprising CoQ10 (CoQ10), and mice treated with cream comprising melatonin+CoQ 10 (aMT+CoQ 10). ***p<0.001 compared to C; +++p<0.001 compared to CoQ10, ###P<0.001 compared to melatonin.
Figure 5:
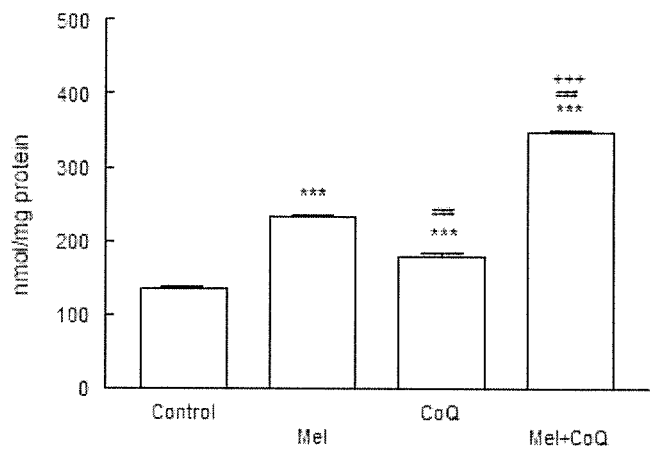
FIG. 5 shows levels of melatonin in mitochondrion of the skin of mice treated with cream comprising melatonin, cream comprising CoQ10, and cream comprising melatonin+CoQ10. Controls (C), mice treated with cream comprising melatonin (aMT), mice treated with cream comprising CoQ10 (CoQ), and mice treated with cream comprising melatonin+CoQ 10 (aMT+CoQ). ***p<0.001 compared to C; +++p<0.001 compared to CoQ10, ###P<0.001 compared to melatonin.

By observing the results obtained in FIGS. 2 and 5, it is shown that melatonin potentiates the movement of CoQ10 into the mitochondrion, and conversely, CoQ10 potentiates the movement of melatonin into said organelle, since both compounds are at a significantly higher amount in the mitochondrion in the group in which they were jointly administered in the cream, compared with the administration of only melatonin or of only CoQ10. FIG. 2 shows that melatonin potentiates the movement of CoQ10 into the mitochondrion. FIG. 5 shows that CoQ10 potentiates the movement of melatonin into the cell in a very significant manner. A concentration of melatonin in the mitochondrion in the presence of CoQ10 is shown to be 4 times greater. These results are confirmed by what is shown in FIGS. 1 and 4, since in the case of FIG. 1, levels of CoQ10 in the cytosol are lower in the group of the joint administration of melatonin and CoQ10, than in the case of CoQ10 administered alone. Therefore, in the case of joint administration, CoQ10 began to be introduced into the mitochondrion from the cytosol. In the case of FIG. 4, CoQ10 potentiates in a very significant manner the movement of melatonin into the cell, and specifically into the mitochondrion. Additionally, despite the fact that CoQ10 increases the movement of melatonin into the mitochondrion, the melatonin continues to be very high in the cytosol, levels of this molecule in the cytosol being much higher when it is administered together with CoQ10 than when it is administered alone.

Figure 3:
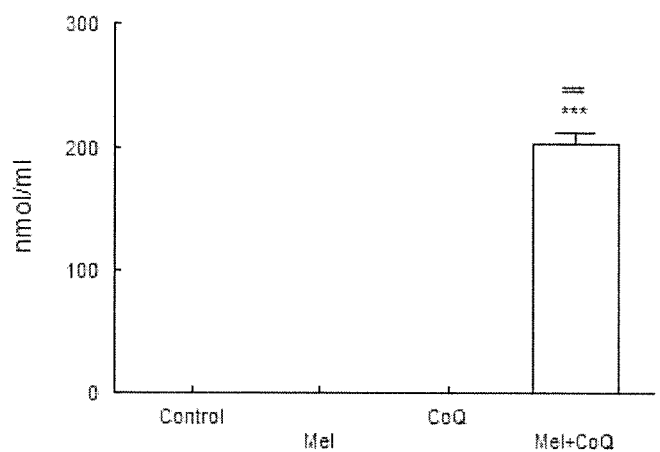
FIG. 3 shows levels of CoQ10 in the plasma of mice treated with cream comprising melatonin, cream comprising CoQ10, and cream comprising melatonin+CoQ10. Controls (C), mice treated with cream comprising melatonin (aMT), mice treated with cream comprising CoQ10 (CoQ), and mice treated with cream comprising melatonin+CoQ 10 (aMT+CoQ). ***$p<0.001$ compared to C; +++$p<0.001$ compared to CoQ10, ###$P<0.001$ compared to melatonin.
Figure 6:
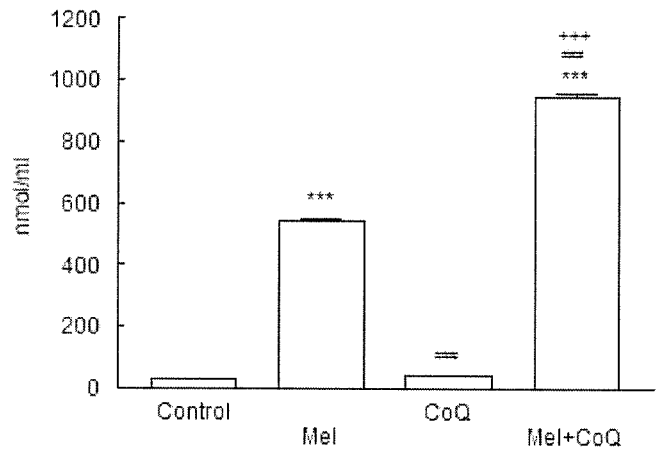
FIG. 6 shows levels of melatonin in the plasma of mice treated with cream comprising melatonin, cream comprising CoQ10, with cream comprising melatonin+CoQ10. Controls (C), mice treated with cream comprising melatonin (aMT), mice treated with cream comprising CoQ10 (CoQ), and mice treated with cream comprising melatonin+CoQ 10 (aMT+CoQ). ***p<0.001 compared to C; +++p<0.001 compared to CoQ10, ###P<0.001 compared to melatonin.

In addition to the movement of CoQ10 into the mitochondrion being potentiated, percutaneous absorption of this molecule is simultaneously favored as melatonin and CoQ10 are administered at the same time. This is reflected in the results shown by the group of joint administration in FIGS. 3 and 6, in which the levels of both CoQ10 and melatonin, respectively, are higher in plasma. Melatonin allows the absorption of CoQ through the dermis, which means that this molecule can reach all of the layers of the skin and does not remain only in the epidermis.

The invention claimed is:
1. A topical composition comprising:
   a) coenzyme Q10 at a concentration of 0.3 to 1.0% w/v with respect to the final composition,
   b) melatonin at a concentration of 1.5 to 3% w/v with respect to the final composition, and
   c) Vitamin E at a concentration of 0.5 to 0.75% w/v with respect to the final composition.
2. The composition according to claim 1 further comprising at least one gelling agent.
3. The composition according claim 1 further comprising at least one pharmaceutically or cosmetically acceptable vehicle, and/or at least one pharmaceutically or cosmetically acceptable excipient or adjuvant.
4. A method for treating cell damage caused by oxidative stress in a patient in need thereof, said method comprising topically administering to the patient the composition according to claim 1.
5. A method for treating a disease presenting cellular aging in a patient in need thereof, said method comprising topically administering to the patient the composition according to claim 1.
6. The method according to claim 5, wherein the disease presenting cellular aging is selected from the group consisting of tumors, cancers, inflammation of tissues and diseases related to the skin.
7. The method according to claim 5, wherein cellular aging is due to exposure to the sun in the skin.
8. A cosmetic method for anti-aging of the skin of a subject, comprising topical application of an effective amount of the composition according to claim 1 to the skin of the subject.
9. The cosmetic method according to claim 8, wherein the aging of the skin is caused by the exposure of the skin to the sun's rays.
10. A sunscreen comprising the composition according to claim 1 and at least one agent acting as filter for UV-B and UV-A rays.

* * * * *